(12) United States Patent
Wender

(10) Patent No.: US 11,668,693 B2
(45) Date of Patent: Jun. 6, 2023

(54) LOADING STATION FOR MICRONAIRE TESTING

(71) Applicant: Uster Technologies AG, Uster (CH)

(72) Inventor: James T. Wender, Seymour, TN (US)

(73) Assignee: Uster Technologies AG, Uster (CH)

( * ) Notice: Subject to any disclaimer, the term of this patent is extended or adjusted under 35 U.S.C. 154(b) by 337 days.

(21) Appl. No.: 17/250,685

(22) PCT Filed: Aug. 26, 2019

(86) PCT No.: PCT/CH2019/000026
§ 371 (c)(1),
(2) Date: Feb. 19, 2021

(87) PCT Pub. No.: WO2020/056529
PCT Pub. Date: Mar. 26, 2020

(65) Prior Publication Data
US 2021/0302406 A1   Sep. 30, 2021

Related U.S. Application Data

(60) Provisional application No. 62/733,722, filed on Sep. 20, 2018.

(51) Int. Cl.
*G01N 33/36* (2006.01)
*G01N 15/08* (2006.01)
*D01G 23/04* (2006.01)
*G01N 1/28* (2006.01)

(52) U.S. Cl.
CPC ........... *G01N 33/362* (2013.01); *D01G 23/04* (2013.01); *G01N 1/286* (2013.01); *G01N 15/08* (2013.01); *D10B 2201/02* (2013.01)

(58) Field of Classification Search
CPC ............ G01N 1/00; G01N 1/28; G01N 1/286; G01N 15/00; G01N 15/08; D01G 23/04; D10B 2201/02
See application file for complete search history.

(56) References Cited

U.S. PATENT DOCUMENTS

| 5,359,880 A * | 11/1994 | Elam .................... G01N 15/08 73/38 |
| 5,892,142 A | 4/1999 | Ghorashi et al. |
| 6,098,454 A | 8/2000 | Ghorashi et al. |
| 6,532,798 B1 | 3/2003 | Shofner et al. |
| 9,016,120 B2 | 4/2015 | Wender et al. |
| 2003/0115935 A1 | 6/2003 | Shofner et al. |
| 2013/0199287 A1 | 8/2013 | Wender et al. |

* cited by examiner

Primary Examiner — Nguyen Q. Ha
(74) Attorney, Agent, or Firm — Rick Barnes

(57) ABSTRACT

A loading station for forming a fiber mass for micronaire testing. The loading station has a hopper for receiving an unformed fiber mass. A forming chamber receives the unformed fiber mass from the hopper. The forming chamber includes a non-movable back wall and a non-movable bottom plate with ports formed therein. The ports draw an airflow from the hopper into the forming chamber. A selectively movable isolation plate isolates the forming chamber from the hopper, and a selectively movable horizontal forming wall horizontally compacts the fiber mass into a desired horizontal cross-section. A selectively movable vertical forming wall vertically compacts the fiber mass into a desired vertical cross-section. A selectively movable plunger presses axially along the shaped fiber mass.

9 Claims, 7 Drawing Sheets

LOADING STATION FOR MICRONAIRE TESTING

FIELD

This application claims rights and priority on prior U.S. provisional patent application Ser. No. 62/733,722 filed 2018 Sep. 20 and prior PCT patent application serial number PCT/CH2019/000026 filed 2019 Aug. 26. This invention relates to the field of textile fiber characteristic measurement. More particularly, this invention relates to micronaire testing. Even more particularly, it relates to a loading station for forming a fiber mass for micronaire testing.

BACKGROUND

Micronaire is a measure of the air permeability of compressed cotton fibers. It is often used as an indication of fiber fineness and maturity. Thus, micronaire is an important fiber property to measure and track. There is a continual need, therefore, for improved fiber micronaire measurement equipment.

U.S. Pat. No. 5,892,142 to Ghorashi describes a fiber micronaire chamber that receives fiber from a fiber stream, where a damper diverts a portion of the fiber stream along conduits that end in the micronaire chamber. Once a desired amount of fiber is collected within the micronaire chamber, the chamber is isolated from further fiber collection and the micronaire measurement is taken. Thus, Ghorashi describes an efficient apparatus for the measurement of micronaire on fibers that are traveling in a stream of fibers.

U.S. Pat. No. 6,532,798 to Shofner describes an instrument with sensors in a gas flow stream that determine the mass of fibers that is delivered to a testing chamber, where a computer terminates the delivery of the fibers to the testing chamber when a predetermined mass set point is reached. The fiber sample is then delivered to a testing chamber.

Both of the above references describe forming the samples of fibers for micronaire testing from flows of fiber streams. However, there is often a need to test the micronaire of non-fluidized fiber samples.

U.S. Pat. No. 9,016,120 to Wender describes a fiber forming apparatus with a fiber sample loader for receiving an amount of unformed fiber. A first lateral forming surface of the fiber sample loader is brought toward a second lateral forming surface of the fiber sample loader and the fiber sample is formed between the first lateral forming surface and the second lateral forming surface to form three sides of the fiber sample. A vertical forming surface of the fiber sample loader is brought down between the first lateral forming surface and the second lateral forming surface and onto the fiber sample to form a fourth side of the fiber sample, thereby forming the fiber sample into an elongate plug having a cross-sectional shape and size that are substantially similar to a cross-sectional shape and size of a micronaire chamber in which the micronaire measurement is to be taken. The plug is inserted into the micronaire chamber with a plunger. This fiber forming apparatus does not always form the fiber sample satisfyingly. Part of the unformed fiber can sometimes stay in an upper region of the fiber sample loader, where it is not taken in by the forming surfaces. Thus, not all of the unformed fiber are formed into the plug. Moreover, such fibers remaining in the fiber sample loader can cause mechanical problems. Hence, frequent maintenance of the fiber forming apparatus has to be performed.

SUMMARY

What is needed, therefore, is a system that tends to reduce issues such as those described above, at least in part.

The above and other needs are met by a loading station for forming a fiber mass for micronaire testing. The loading station has a hopper for receiving an unformed fiber mass. A forming chamber receives the unformed fiber mass from the hopper. The forming chamber includes a non-movable back wall and a non-movable bottom plate with ports formed therein. The ports draw an airflow from the hopper into the forming chamber. A selectively movable isolation plate isolates the forming chamber from the hopper, and a selectively movable horizontal forming wall horizontally compacts the fiber mass into a desired horizontal cross-section. A selectively movable vertical forming wall vertically compacts the fiber mass into a desired vertical cross-section. A selectively movable plunger presses axially along the shaped fiber mass.

In some embodiments, the plunger moves the shaped fiber mass out of the forming chamber prior to micronaire testing. In some embodiments, the forming chamber is adapted for use as a micronaire testing chamber and the selectively movable plunger assists in compacting the shaped fiber mass within the forming chamber while micronaire readings are taken on the shaped fiber mass. In some embodiments, an intersection between the back wall and the bottom plate comprises a quarter-circular cross-section. In some embodiments, the horizontal forming wall in a vicinity of the bottom plate comprises a quarter-circular cross-section. In some embodiments, the vertical forming wall comprises a semi-circular cross-section. In some embodiments, the desired horizontal cross-section and the desired vertical cross-section jointly form a circular cross-section. In some embodiments, the loading station further comprises a vacuum source arranged underneath the bottom plate for drawing the airflow from the hopper through the ports. In some embodiments, the ports in the non-movable bottom plate are adapted to take pressure readings during a micronaire measurement of the fiber mass within the forming chamber.

The hopper, the isolation plate, and the ports according to the present invention function synergistically to efficiently load the fiber mass into the forming chamber. The hopper defines locally the insertion of the fiber mass into the forming chamber, such that the fiber mass is deposited exactly in the destination area of the forming chamber. The isolation plate defines temporally the insertion of the fiber mass into the forming chamber, such that the fiber mass is delivered to the forming chamber only during an envisaged time slot. The airflow drawn by the ports into the forming chamber conveys all of the fiber mass to a bottom region of the forming chamber, where it is reliably formed into the desired cross-section. Thus, no fibers remain undesirably in the loading station. Maintenance time and effort is reduced. The adaptation of the forming chamber to also function as a micronaire testing chamber simplifies the overall design of the apparatus, and reduces to some degree the time that is required to perform a loading, forming, and testing cycle on a given sample of the fiber mass.

BRIEF DESCRIPTION OF DRAWINGS

Further advantages of the invention are apparent by reference to the detailed description when considered in conjunction with the figures, which are not to scale so as to more clearly show the details, wherein like reference numbers indicate like elements throughout the several views, and wherein.

DESCRIPTION OF EMBODIMENTS

Figure 1:
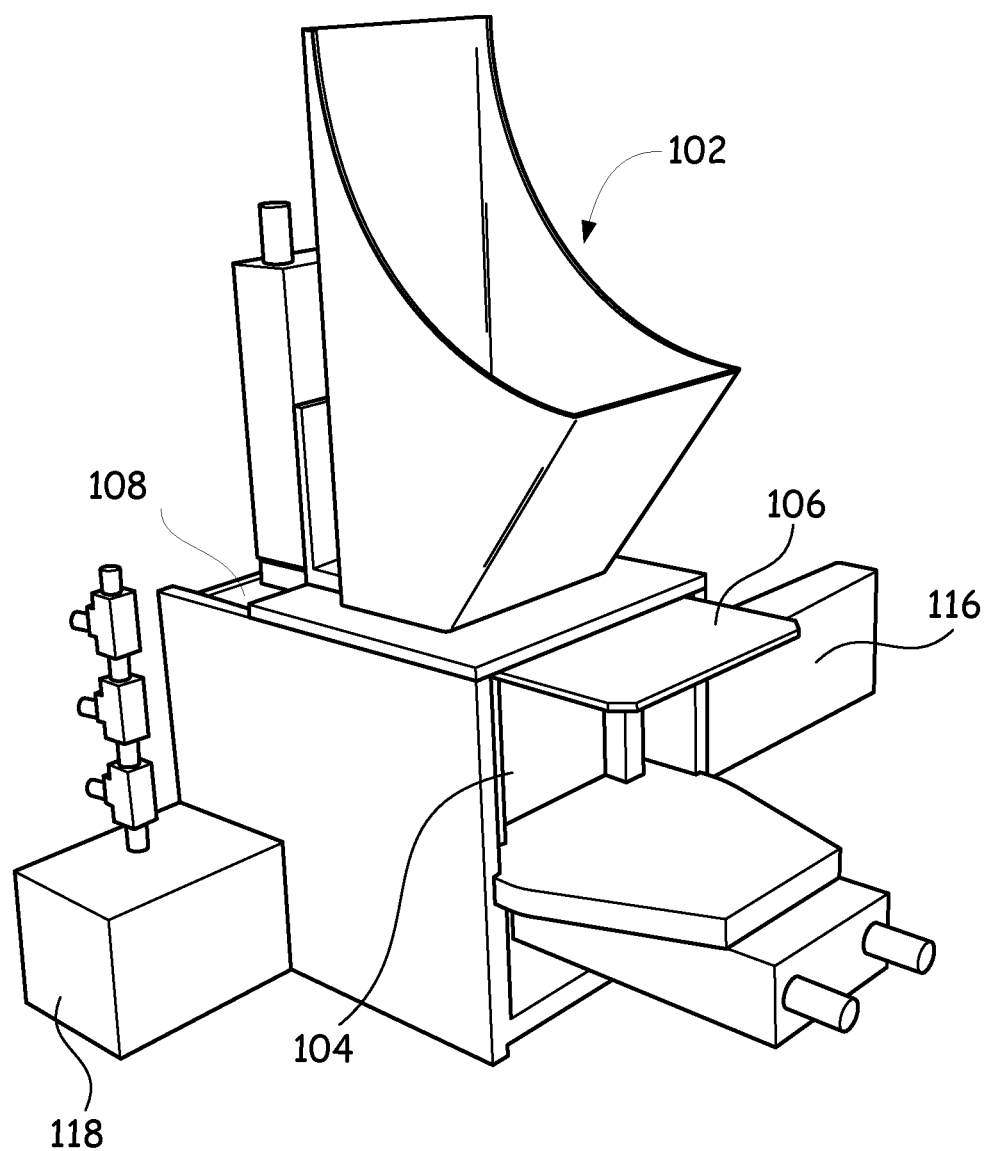
FIG. 1 is a first partial perspective view of a fiber micronaire loader according to an embodiment of the present invention.

With reference now to FIG. 1, there are depicted portions of a micronaire loading system 100, such as can be used to receive a mass of fiber 112 (see FIG. 4) and form it into a cylindrical plug that is suitable for insertion into a cylindrical micronaire testing chamber of substantially the same size. By preforming the fiber mass 112 into a plug having substantially the same diameter and length as the micronaire testing chamber, the cycling speed of the micronaire measurements on successive fiber masses 112 or fiber samples can be generally increased. A separate micronaire testing chamber is not shown in the drawings; however, a micronaire chamber that is separate from the micronaire forming chamber as described herein, and micronaire measurements, are described and depicted in detail in U.S. Pat. No. 9,016,120, which is incorporated herein by reference.

Figure 2:
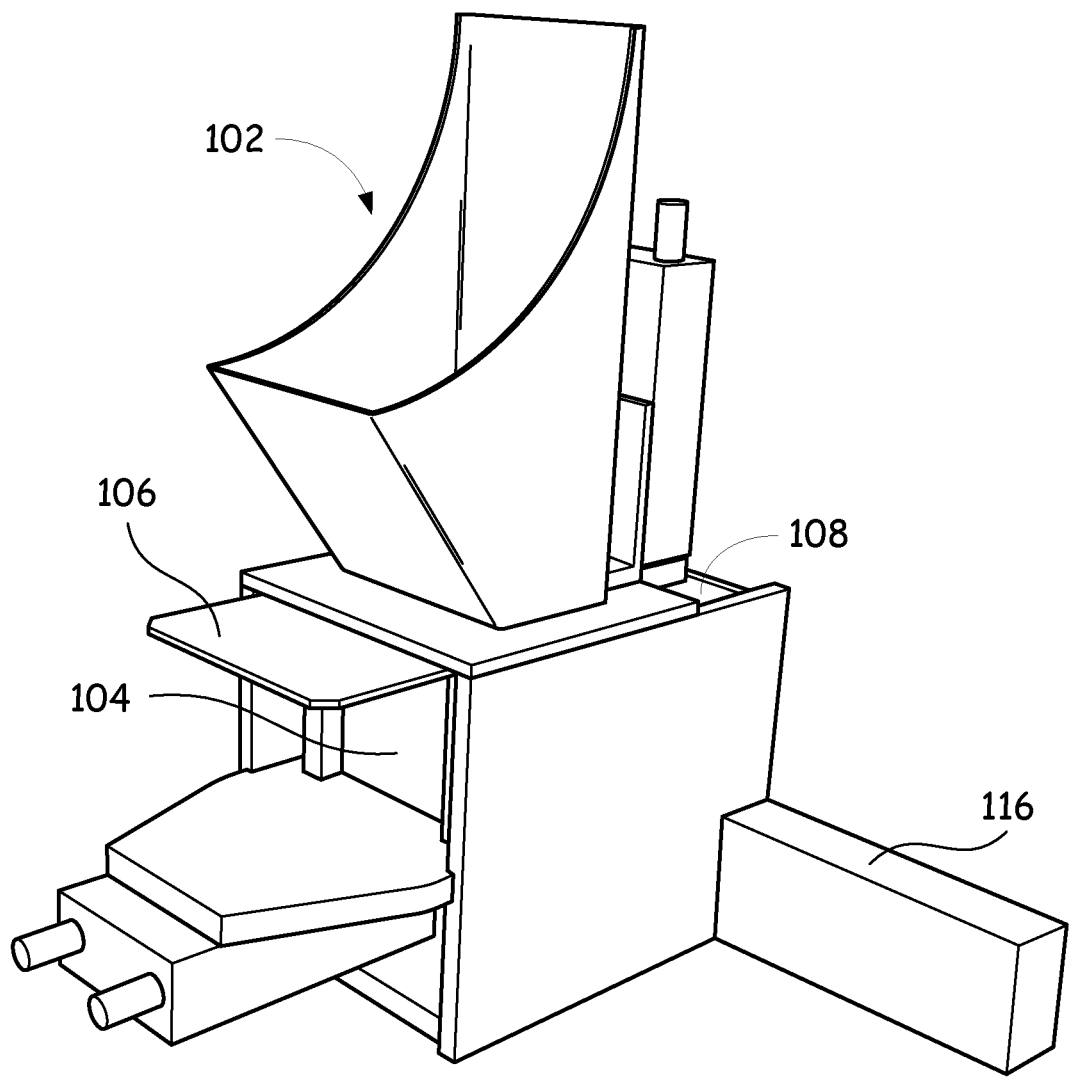
FIG. 2 is a second partial perspective view of a fiber micronaire loader according to an embodiment of the present invention.

The loading station 100 includes a hopper 102 for receiving the fiber mass 112. Actuators move a horizontal forming wall 104 and a sample isolation plate 106 into a receiving position and a forming position. The horizontal forming wall 104 serves to form the fiber mass 112 in the horizontal direction. Another actuator moves a vertical forming wall 108 into a receiving position and a forming position. The vertical forming wall 108 serves to form the fiber mass 112 in the vertical direction. A plunger 116 has operation as described in more detail below. FIG. 2 depicts these elements from a different perspective.

Figure 3:
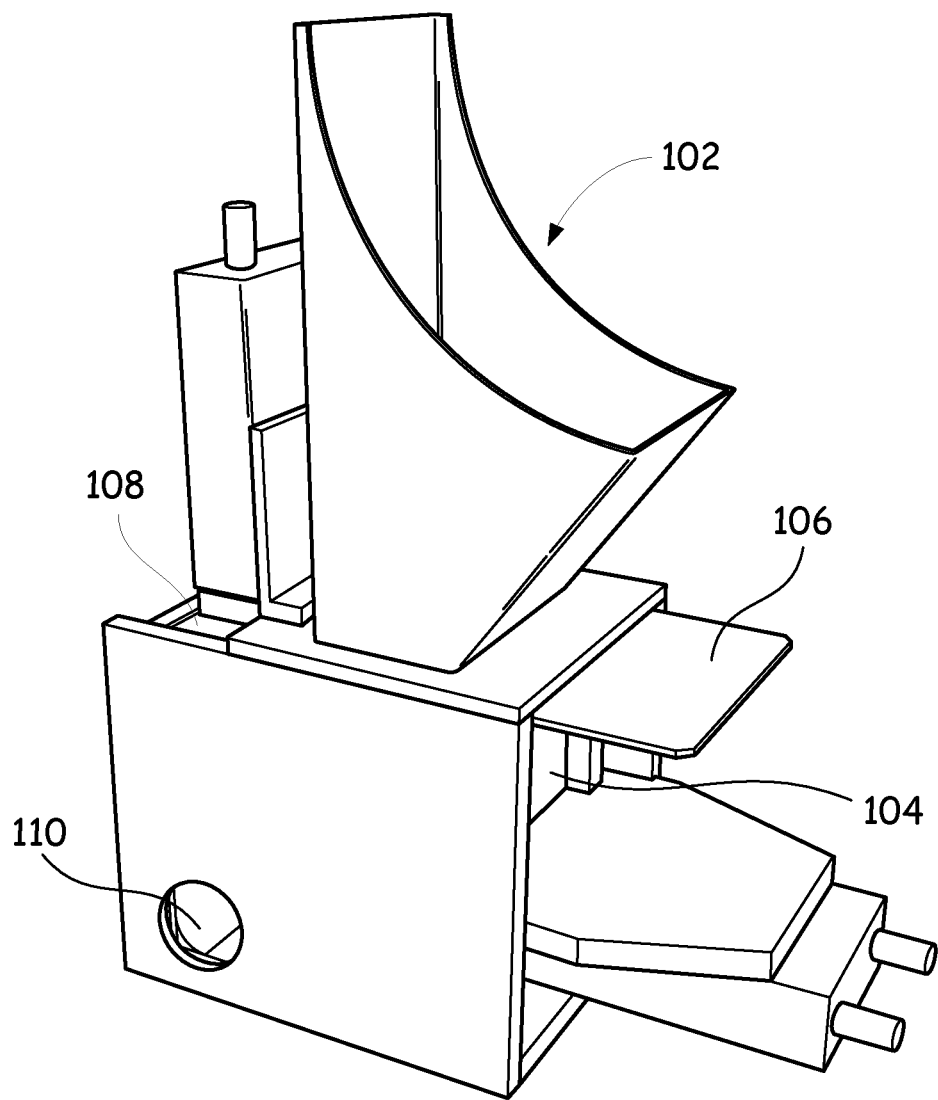
FIG. 3 is a third partial perspective view of a fiber micronaire loader according to an embodiment of the present invention.

FIG. 3 depicts the loading system 100 with some of the system elements removed, and depicting an orifice 110. A similar orifice is disposed on the opposing side of the loading station 100 in some embodiments. The orifice 110 is in one embodiment the approximate diameter of the micronaire testing chamber. In one embodiment, the plunger 116 extends through the orifice 110 as depicted to move the fiber plug into the micronaire testing chamber that is affixed to the other side of the loading station 100. In another embodiment, the micronaire testing chamber is affixed to the depicted side of the loading station 100, and the plunger 116 comes through the loading station from the other side. In still another embodiment, the forming chamber is identical with the micronaire testing chamber. In any case, the direction of movement of the plunger 116 is perpendicular to the direction of movement of the horizontal forming wall 104 and to the direction of movement of the vertical forming wall 108.

Figure 4:
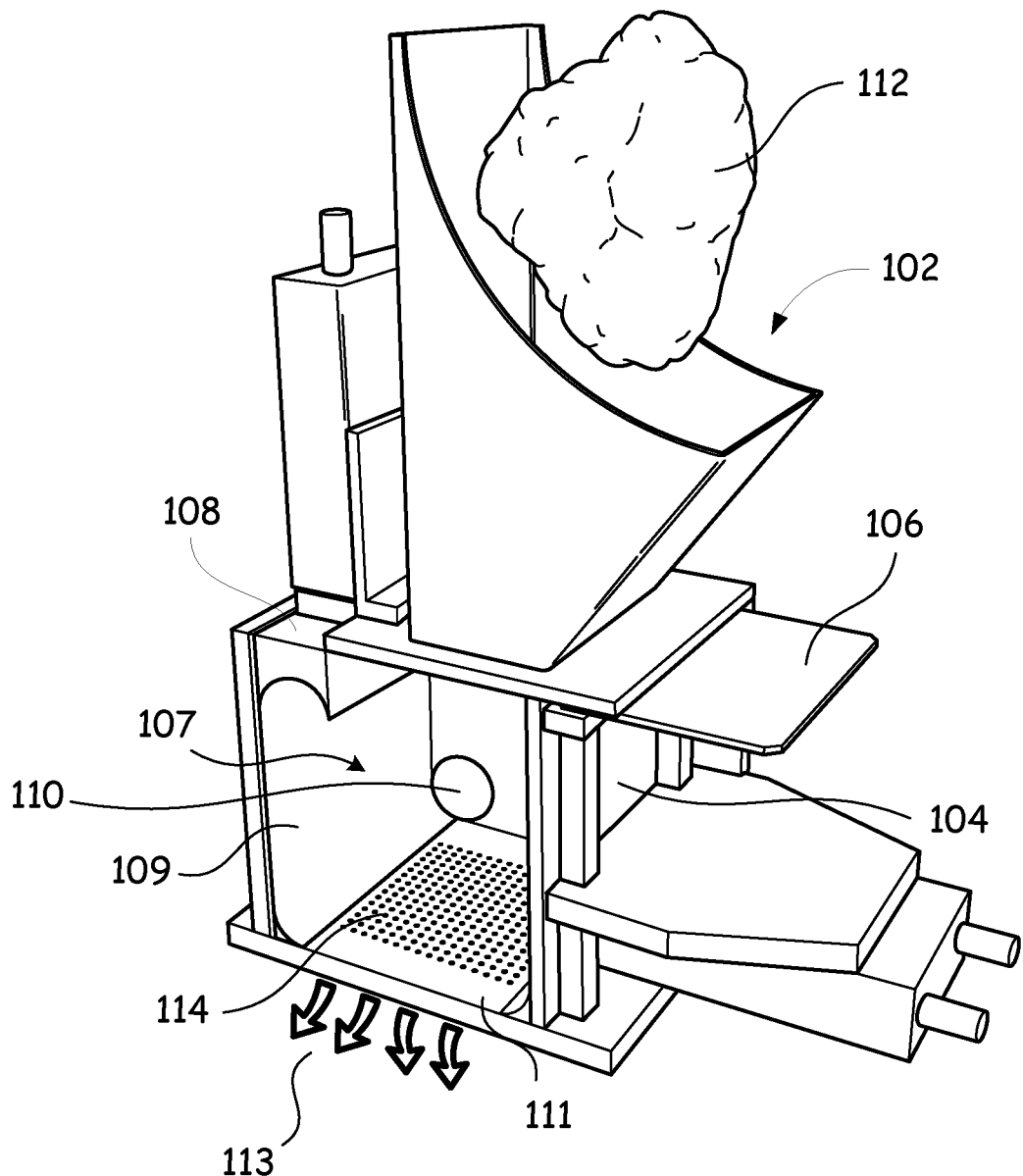
FIG. 4 is a cutaway partial perspective view of a fiber micronaire loader according to an embodiment of the present invention, showing a fiber mass in a first position.

With reference now to FIG. 4, there is depicted a fiber mass 112 entering the hopper 102. The horizontal forming wall 104, the vertical forming wall 108, and the sample isolation plate 106 are all retracted into their receiving positions, as depicted, and the fiber mass 112 can fall through the hopper 102 and directly into a forming chamber 107.

The forming chamber 107 comprises a non-movable back wall 109 and a non-movable bottom plate 111. An intersection between the back wall 109 and the bottom plate 111 can have a quarter-circular cross-section; the horizontal forming wall 104 in a vicinity of the bottom plate 111 can have a quarter-circular cross-section; and the vertical forming wall (108) can have a semi-circular cross-section. Thus, in the forming position shown in FIG. 7, the forming chamber 107 has a circular cross-section. In this embodiment, the desired horizontal cross-section and the desired vertical cross-section of the compacted fiber mass 112 jointly form a circular cross-section.

Figure 5:
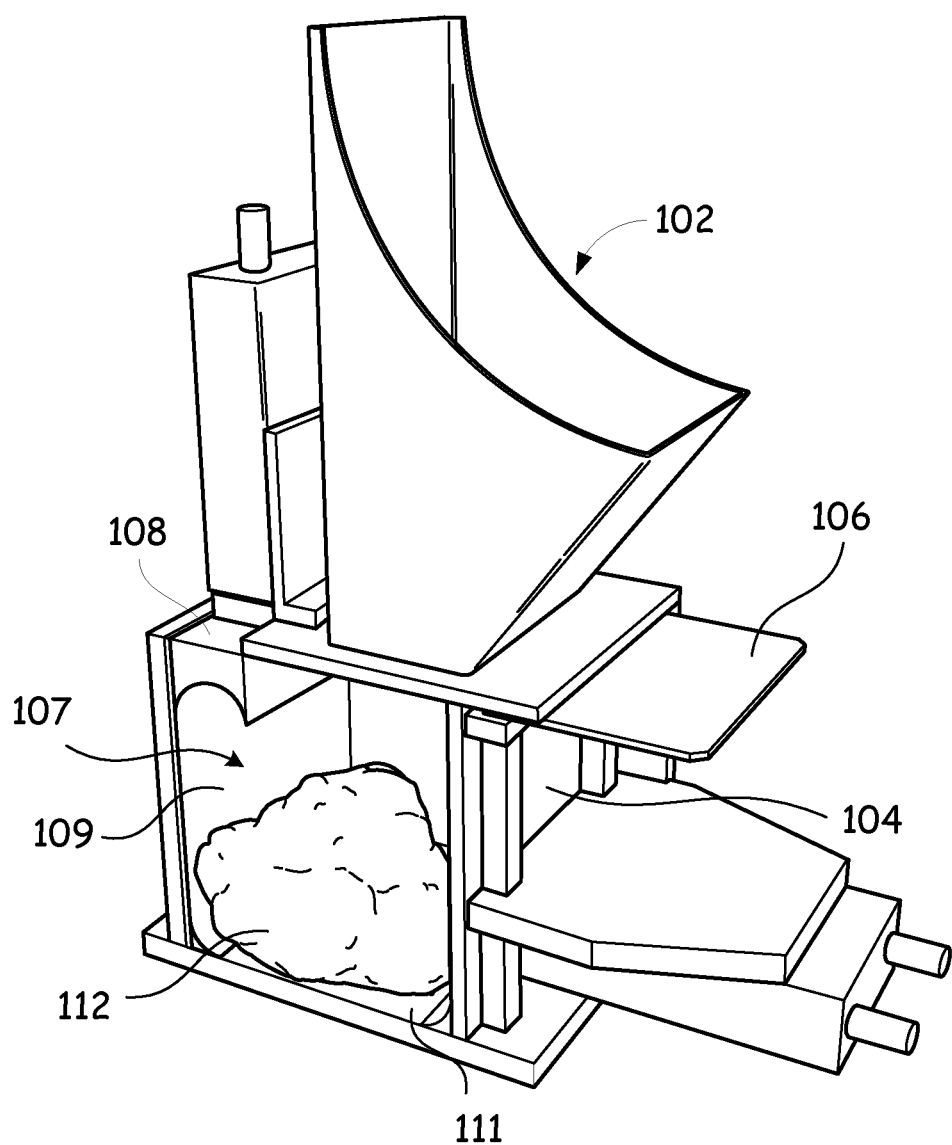
FIG. 5 is a cutaway partial perspective view of a fiber micronaire loader according to an embodiment of the present invention, showing a fiber mass in a second position.

Ports 114 formed in the bottom of the forming chamber 107 are connected to a vacuum source arranged underneath the bottom plate 111 so as to draw an airflow from the hopper 102 through the perforated bottom plate of the forming chamber 107. This assists the fiber mass 112 to completely enter the forming chamber 107, as depicted in FIG. 5, so that it does not get caught and retained by any of the elements near the top of the forming chamber 107.

Figure 6:
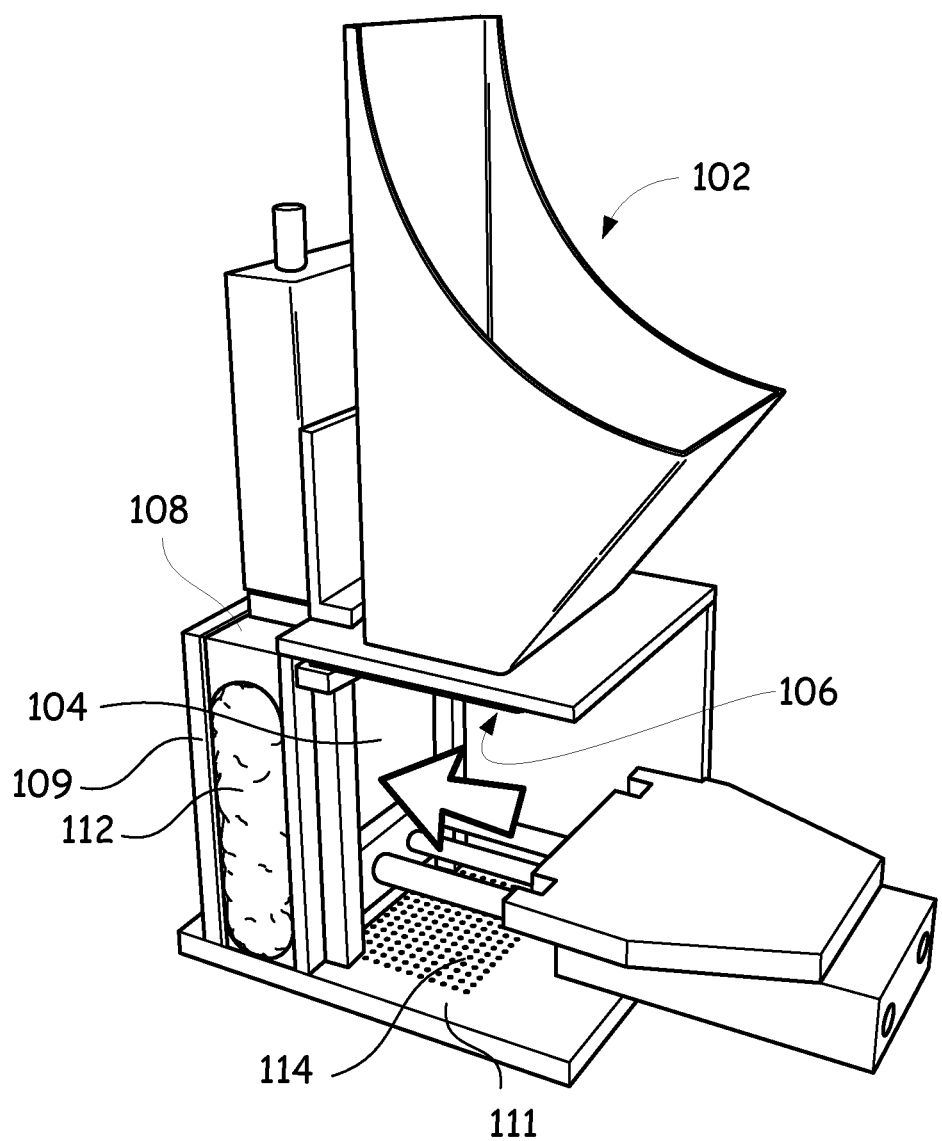
FIG. 6 is a cutaway partial perspective view of a fiber micronaire loader according to an embodiment of the present invention, showing a fiber mass in a third position.

The horizontal forming wall 104 is then brought into the inserted forming position, as depicted in FIG. 6. In one embodiment, the sample isolation plate 106 moves with the horizontal forming wall 104 so that the hopper 102 is isolated from the forming chamber 107, and thereby any fiber samples 112 that might be newly inserted into the hopper 102 are not allowed to fall into the outer workings of the loading station 100, such as behind the horizontal forming wall 104, or into the fiber mass 112 that was already drawn into the fiber forming chamber 107. In some embodiments, at some point in time before, during or after the movement of the horizontal forming wall 104, the vacuum drawn through the ports 114 is discontinued.

At this point, the fiber mass 112 has been formed to have a horizontal cross-section that is substantially the same as the diameter of the micronaire testing chamber.

Figure 7:
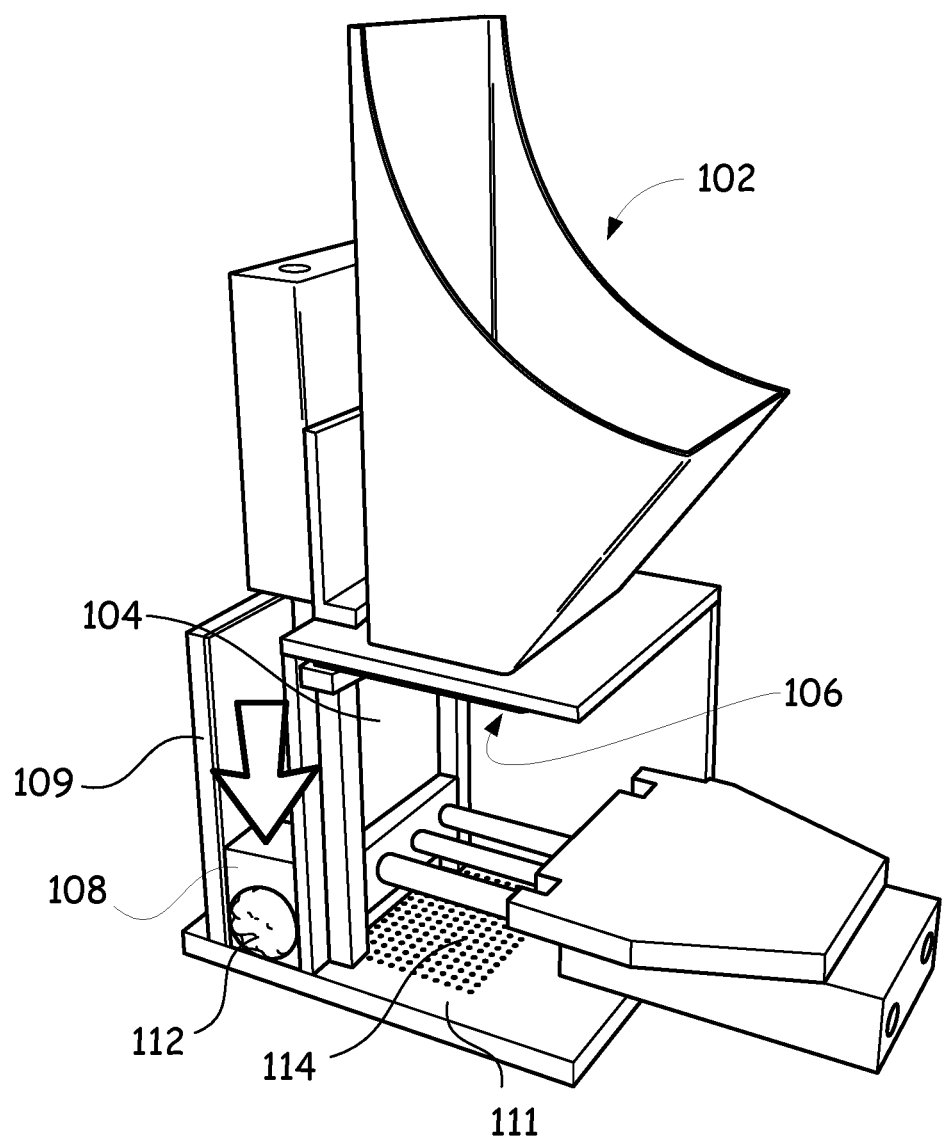
FIG. 7 is a cutaway partial perspective view of a fiber micronaire loader according to an embodiment of the present invention, showing a fiber mass in a fourth position.

The vertical forming wall 108 is then brought down from the retracted loading position into the inserted forming position, as depicted in FIG. 7, which compacts the fiber mass 112 such that the vertical cross-section of the compacted fiber mass 112 is substantially the same as the diameter of the micronaire testing chamber. At this point, the fiber mass 112 has been formed into a cylindrical plug having substantially the same diameter as the micronaire testing chamber. The plug also has substantially the same length as the micronaire testing chamber, because the width of the forming chamber 107 is designed to be substantially the same as the length of the micronaire testing chamber.

There are now two embodiments for micronaire processing of the fiber mass 112. In the first embodiment, the fiber mass 112 is pressed by the plunger 116 through the loading system 100 and into the micronaire testing chamber that is externally disposed but attached to the loader 100. As introduced above, the plunger 116 and the micronaire testing chamber are mounted on opposing sides of the loading station 100, but it does not matter on which side either is mounted. The plug 112 is disposed of on the opposite end of the micronaire testing chamber from which it was loaded, and the process is repeated with successive fiber masses 112.

In the second embodiment, the forming chamber 107 is the micronaire testing chamber, and the micronaire readings are taken, such as at the micronaire head 118, as the plunger 116 advances and compresses the fiber sample 112 within the combined forming chamber 107/micronaire testing chamber. Micronaire measurements are described in detail in U.S. Pat. No. 9,016,120.

The present invention different from U.S. Pat. No. 9,016,120 in several ways. Various embodiments of the present invention include the hopper 102 to receive the fiber mass 112, the isolation plate 106 to isolate the hopper 102 from the forming chamber 107, the ports 114 in the bottom plate 111 to draw the fiber mass 112 down into the forming chamber 107, and the ability to use the forming chamber 107 as a micronaire testing chamber. U.S. Pat. No. 9,016,120 describes none of these elements.

The hopper 102, isolation plate 106, and ports 114 function synergistically to efficiently load the fiber mass 112 into the forming chamber 107. The adaptation of the forming chamber 107 to also function as a micronaire testing chamber simplifies the overall design of the apparatus 100, and reduces to some degree the time that is required to perform a loading, forming, and testing cycle on a given sample of the fiber mass 112.

The foregoing description of embodiments for this invention has been presented for purposes of illustration and description. It is not intended to be exhaustive or to limit the invention to the precise form disclosed. Obvious modifications or variations are possible in light of the above teachings. The embodiments are chosen and described in an effort to provide illustrations of the principles of the invention and its practical application, and to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

REFERENCE SIGNS LIST

100 Loading station
102 Hopper
104 Horizontal forming wall
106 Isolation plate
107 Forming chamber/Micronaire testing chamber
108 Vertical forming wall
109 Back wall
110 Orifice
111 Bottom plate
112 Fiber mass
113 Airflow
114 Ports
116 Plunger
118 Micronaire head

The invention claimed is:

1. A loading station for forming a fiber mass for micronaire testing, the loading station having:
    a forming chamber for receiving an unformed fiber mass, the forming chamber comprising,
        a non-movable back wall,
        a non-movable bottom plate,
        a selectively movable horizontal forming wall for horizontally compacting the fiber mass into a desired horizontal cross-section, and
        a selectively movable vertical forming wall for vertically compacting the fiber mass into a desired vertical cross-section,
    a selectively movable plunger for pressing axially along the shaped fiber mass,
    a hopper for receiving the unformed fiber mass and delivering the unformed fiber mass to the forming chamber,
    a selectively movable isolation plate for isolating the forming chamber from the hopper, and
    ports formed in the non-movable bottom plate, the ports for drawing an airflow from the hopper into the forming chamber.

2. The loading station of claim 1, wherein the plunger moves the shaped fiber mass out of the forming chamber prior to micronaire testing.

3. The loading station of claim 1, wherein the forming chamber is adapted for use as a micronaire testing chamber and the selectively movable plunger assists in compacting the shaped fiber mass within the forming chamber while micronaire readings are taken on the shaped fiber mass.

4. The loading station of claim 1, wherein an intersection between the back wall and the bottom plate comprises a quarter-circular cross-section.

5. The loading station of claim 1, wherein the horizontal forming wall in a vicinity of the bottom plate comprises a quarter-circular cross-section.

6. The loading station of claim 1, wherein the vertical forming wall comprises a semi-circular cross-section.

7. The loading station of claim 1, wherein the desired horizontal cross-section and the desired vertical cross-section jointly form a circular cross-section.

8. The loading station of claim 1, further comprising a vacuum source arranged underneath the bottom plate for drawing the airflow from the hopper through the ports.

9. The loading station of claim 1, wherein the ports in the non-movable bottom plate are adapted to take pressure readings during a micronaire measurement of the fiber mass within the forming chamber.

* * * * *